United States Patent
Lalka et al.

(10) Patent No.: US 6,511,325 B1
(45) Date of Patent: Jan. 28, 2003

(54) AORTIC STENT-GRAFT CALIBRATION AND TRAINING MODEL

(75) Inventors: Stephen G. Lalka, Carmel; James B. Beck, Indianapolis, both of IN (US)

(73) Assignee: Advanced Research & Technology Institute, Bloomington, IN (US)

( * ) Notice: Subject to any disclaimer, the term of this patent is extended or adjusted under 35 U.S.C. 154(b) by 0 days.

(21) Appl. No.: 09/072,431

(22) Filed: May 4, 1998

(51) Int. Cl.[7] .............................................. G09B 23/28
(52) U.S. Cl. ...................................... 434/272; 434/267
(58) Field of Search ................................ 434/272, 262, 434/267; 308/207

(56) References Cited

U.S. PATENT DOCUMENTS

| | | | | |
|---|---|---|---|---|
| 3,271,880 A | * | 9/1966 | Sackler | 434/272 |
| 3,638,709 A | * | 2/1972 | Brown | 434/296 |
| 4,922,915 A | * | 5/1990 | Arnold | 128/653 R |
| 5,052,934 A | * | 10/1991 | Carey | 434/268 |
| 5,055,051 A | * | 10/1991 | Duncan | 434/262 |
| 5,112,228 A | * | 5/1992 | Zouras | 434/272 |
| 5,115,394 A | | 5/1992 | Walters | |
| 5,236,363 A | * | 8/1993 | Sandrik | 434/267 |
| 5,551,881 A | | 9/1996 | Henderson et al. | |
| 5,741,478 A | * | 4/1998 | Osborne | 424/9.52 |
| 5,799,059 A | * | 8/1998 | Stembridge | 378/207 |
| 5,844,965 A | * | 12/1998 | Galkin | 378/207 |
| 5,860,923 A | * | 1/1999 | Lenker | 600/433 |
| 5,908,387 A | | 6/1999 | LeFree et al. | |
| 5,923,727 A | | 7/1999 | Navab | |

OTHER PUBLICATIONS

Chong, et al, "A Prototype Simulator for Endovascular Repair of Abdominal Aortic Aneurysms", Eur. J. Vasc. Endovasc. Surg., 13, 330–333, Mar. 1997.*

Lui, et al., "Measurement of Phantom Tortuous Abdominal Aortic Ansurysm Length for Intraluminal Graft Placement by Using MR Angiography", abstract presented at Radiologic Society of North America Annual Meeting, Nov. 27, 1995.

Chong, et al., "A Prototype Simulator for Endovascular Repair of Abdominal Aortic Aneurysms", Eur J. Vasc Endovasc Surg., 13, 330–333, Mar. 13, 1997.

* cited by examiner

Primary Examiner—Derris H. Banks
Assistant Examiner—Kurt Fernstrom
(74) Attorney, Agent, or Firm—Dann, Dorfman, Herrell and Skillman, P.C.

(57) ABSTRACT

An aortic stent-graft model is provided. A hollow Y-frame is cast from polyurethane to form a core. After silicone aortic wall thickness and aneurysmal segments are applied to the contour of the core, the polyurethane core is removed to leave a hollow aortic model of silicone. Marking indicia are applied to the aortic model to effect selected dimensional measurements. The model can be utilized to calibrate the equipment of testing modalities such as contrast aortography (CA), spiral computed tomography (CT), magnetic resonance imaging (MRI), and intravascular ultrasonography (IVUS). Dimensional measurements from the marking indicia are compared to corresponding images of the model to detect any variation needed for calibration. An aortic stent-graft model can also be utilized to simulate introduction of a guidewire and catheter for deployment of a stent for repair of an abdominal aortic aneurysm (AAA).

29 Claims, 8 Drawing Sheets

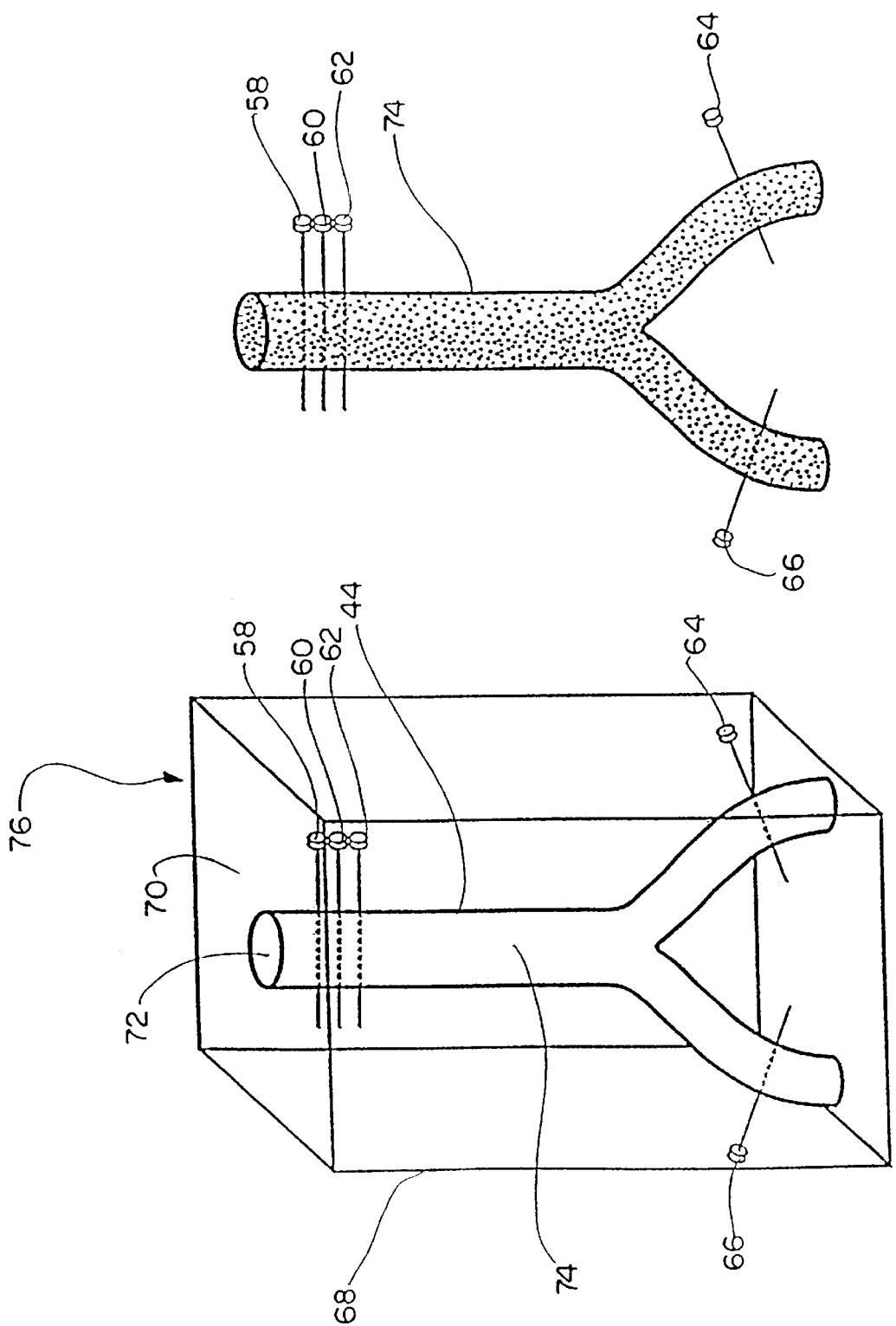

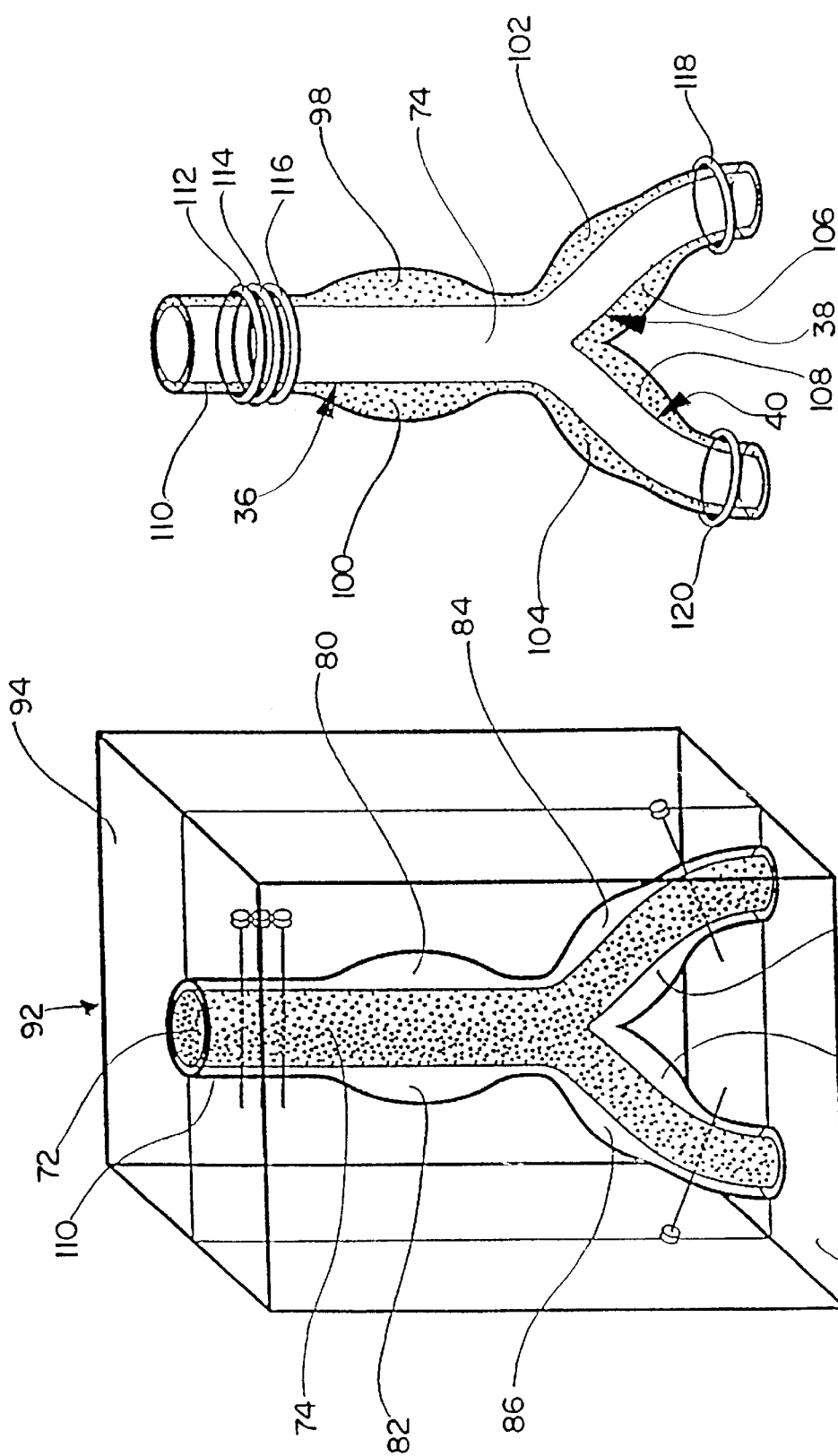

AORTIC STENT-GRAFT CALIBRATION AND TRAINING MODEL

FIELD OF THE INVENTION

The present invention relates to an aortic stent-graft calibration model for the calibration of different imaging modalities and to a stent-graft training model for enabling pre-operative surgical practice for successful stent deployment for repair of an abdominal aortic aneurysm (AAA).

BACKGROUND OF THE INVENTION

The need for repair of an abdominal aortic aneurysm (AAA) in patients has been recognized for many years in the medical field. Abdominal aortic aneurysms (AAA) affect a significant portion of the elderly population. Surgical repair of an abdominal aortic aneurysm (AAA) has a much higher mortality rate than less invasive techniques, such as deployment of a stent through a femoral artery.

Essential to the successful placement of a stent for repair of an abdominal aortic aneurysm (AAA) are pre-operative imaging modalities. The four most utilized imaging modalities in the medical field are contrast aortography (CA), spiral computed tomography (CT), magnetic resonance imaging (MRI), and intravascular ultrasonography (IVUS).

These four imaging modalities assess the diameter of the aneurysmal portions of the aortic system, the diameter and length of the nonaneurysmal proximal neck for anchoring the stent, the diameter and length of the distal aortic/iliac neck, and the total length of the prosthesis required for spanning the length of the aneurysm with fixation into normal arterial tissue proximally and distally of the aneurysm. Any inaccuracy in the equipment of the imaging modalities may adversely affect the successful repair of the abdominal aortic aneurysm (AAA) in a patient and increase the risk for major abdominal surgery with its associated mortality rate.

Due to the use of the four imaging modalities in the repair of an abdominal aortic aneurysm (AAA) in a patient, there is a need for accurately calibrating the equipment of all four imaging modalities to insure successful deployment of the stent. Additionally, it is highly desirable for training purposes to simulate the introduction of a guidewire and catheter for deployment of the stent for repair of an abdominal aortic aneurysm (AAA) on a model before performing the procedure on a patient. The present invention provides a calibration model that can be utilized to calibrate the equipment of all four imaging modalities as well as a training model to simulate stent deployment before the procedure is performed on a patient.

SUMMARY OF THE INVENTION

In accordance with the present invention, an aortic stent-graft calibration model is provided for the calibration of the equipment of four widely utilized testing modalities. In addition, an aortic stent-graft training model is provided for effective simulation of deployment of a stent for repair of an abdominal aortic aneurysm (AAA).

In general, the aortic stent-graft calibration model provides an aortic model with aneurysms constructed of a suitable material to permit imaging of the model from a desired imaging modality such as CA, CT, MRI or IVUS. In order to permit calibration of the imaging apparatus used in the selected modalities, the calibration model includes reference indicia at selected locations to provide fixed spatial measurements on the model. The reference indicia are selected so that the indicia are discernable in the image of the model. After the model has been imaged, the actual spatial measurements from the model can be compared to corresponding spatial measurements of the images of the reference indicia taken from the image of the model to detect any difference between the actural locations of the reference indicia on the model and the image locations of the indicia from the model image. In a specific embodiment of the present invention, the aortic stent-graft calibration model comprises a hollow, tubular Y-shaped core having interior and exterior surfaces conforming to the desired shape of a predetermined aorta with selectively positioned and sized aneurysms. The core is comprised of silicone to permit accurate imaging by at least one imaging modality and desirably multiple imaging modalities. An external frame holds the core in a fixed position. The frame is made from a simulated material that does not smash or obliterate the core during imaging or at least is distinguishable from the core in a selected imaging modality. For this purpose, the tubular core of the aortic stent-graft calibration model is mounted in a clear block of suitable material for imaging by the desired imaging modality. For example, the block may be in the form of an acrylic container filled with silicone gel for encasing and suspending the silicone core. To enable the model to be used in calibration of imaging modalities, marking indicia in the form of marking rings are provided at selected locations on the model as reference points for dimensional measurements for comparison to corresponding points on images obtained by the selected imaging modality.

The aortic stent-graft calibration model is produced in a series of steps. First, a rigid skeleton or Y-frame is assembled from hollow plastic piping encased in rubber tubing. The Y-frame is repeatedly dipped in melted wax to achieve a uniform thickness over the contour of the Y-frame. Holes are then made through selected locations of the Y-frame to mark the sites for reference indicia used to acquire dimension measurements and to obtain actual length measurements.

A one-piece silicone mold is formed about the wax covered Y-frame. The Y-frame is then removed from the one-piece silicone mold and a solid polyurethane core is cast from the mold. Wall thickness and aneurysmal segments are then applied to the outer contour of the polyurethane core with melted wax. A two-piece mold of polyurethane is formed about the polyurethane core and the applied wall thickness and aneurysmal segments of wax. The polyurethane core, together with the applied wall thickness and aneurysmal segments of wax, is removed from the two-piece polyurethane mold. The applied wall thickness and aneurysmal segments of wax are removed from the polyurethane core and the wax-coated polyurethane core is placed back in the two-piece polyurethane mold. The space where the wall thickness and aneurysmal segments of wax previously existed is filled with silicone. The polyurethane core with the applied wall thickness and aneurysmal segments of silicone is removed from the mold. The polyurethane core is then removed leaving a hollow tubular Y-shaped core of silicone wall thickness and aneurysmal segments.

The aortic stent-graft calibration model can be utilized to calibrate the equipment of various imaging modalities such as contrast aortography (CA), spiral computed tomography (CT), magnetic resonance imaging (MRI), and intravascular ultrasonography (IVUS). First, reference indicia are applied to the model at the locations corresponding, or at least correlating, to the marked sites made on the initial skeleton. For example, marking rings are attached to selected locations on the model in positions related to the locations of the marked sites on the skeleton. The marking indicia are then filled with contrast agents to permit accurate imaging by the different testing modalities.

The four imaging modalities are then performed on the model. Selected measurements obtained from the acquired images of the referenced indicia of the model from the imaging modalities are compared to the actual dimensions from the model. The equipment of each imaging modality can then be calibrated accordingly.

A model in accordance with the present invention can also be utilized as an aortic stent-graft training model to simulate introduction and placement of a guidewire and catheter for deployment of a stent for repair of an abdominal aortic aneurysm (AAA). In general, the training model comprises two mating halves defining an inner lumen having a contoured inner wall surface in the shape of an aorta with selectively positioned aneurysms. During simulation, a stent can be deployed in the lumen of the model through use of the guidewire and catheter. The model can then be separated into two pieces so that the exact location of the stent may be checked by direct inspection of the model. By opening the model, the stent may also be retrieved for additional practice.

In a specific embodiment of the invention, the aortic stent-graft training model includes two mating halves each providing one half of a hollow, tubular Y-shaped core configured in the shape of a predetermined aorta with selectively positioned and sized aneurysmal segments. An external framing structure is provided for the core. For this purpose, the core of the aortic stent-graft training model is mounted in two mating blocks. The model halves are openable to permit stent retrieval after a practice deployment of the stent in the core of the model. The two mating halves of the model may be formed from a suitable material so that the blocks may be held together by suction. When the two halves are pressed together, the hollow core is accessible from the exterior of the model to permit access to the lumen of the core for deployment of a stent. The hollow core of each mating half has an arterial wall thickness and aneurysmal segments. The inner contour of each core registers with the inner contour of the other core to provide proper alignment of the aorta and the aneurysmal segments. For this purpose, the core of the model is hollow; the blocks are in the form of translucent acrylic containers filled with polyurethane.

BRIEF DESCRIPTION OF THE DRAWINGS

The foregoing summary, as well as the following detailed description of the preferred embodiments of the present invention, will be better understood when read in conjunction with the accompanying drawings, in which:

FIG. 4 is a schematic front perspective view of a mold of silicone elastomer formed from the coated rigid Y-frame shown in FIG. 3 to cast a solid polyurethane core after the Y-frame has been removed;

FIG. 5 is a schematic front perspective view of the solid polyurethane core removed from a mold;

FIG. 8 is a schematic front perspective view of a two-piece polyurethane mold formed about the solid core coated with wall thickness and aneurysmal segments as shown in FIG. 7;

FIG. 9 is a schematic front perspective view of the solid polyurethane core with silicone aortic wall thickness and aneurysmal segments coated thereon removed from the mold shown in FIG. 8;

DETAILED DESCRIPTION OF THE INVENTION

Figure 10:
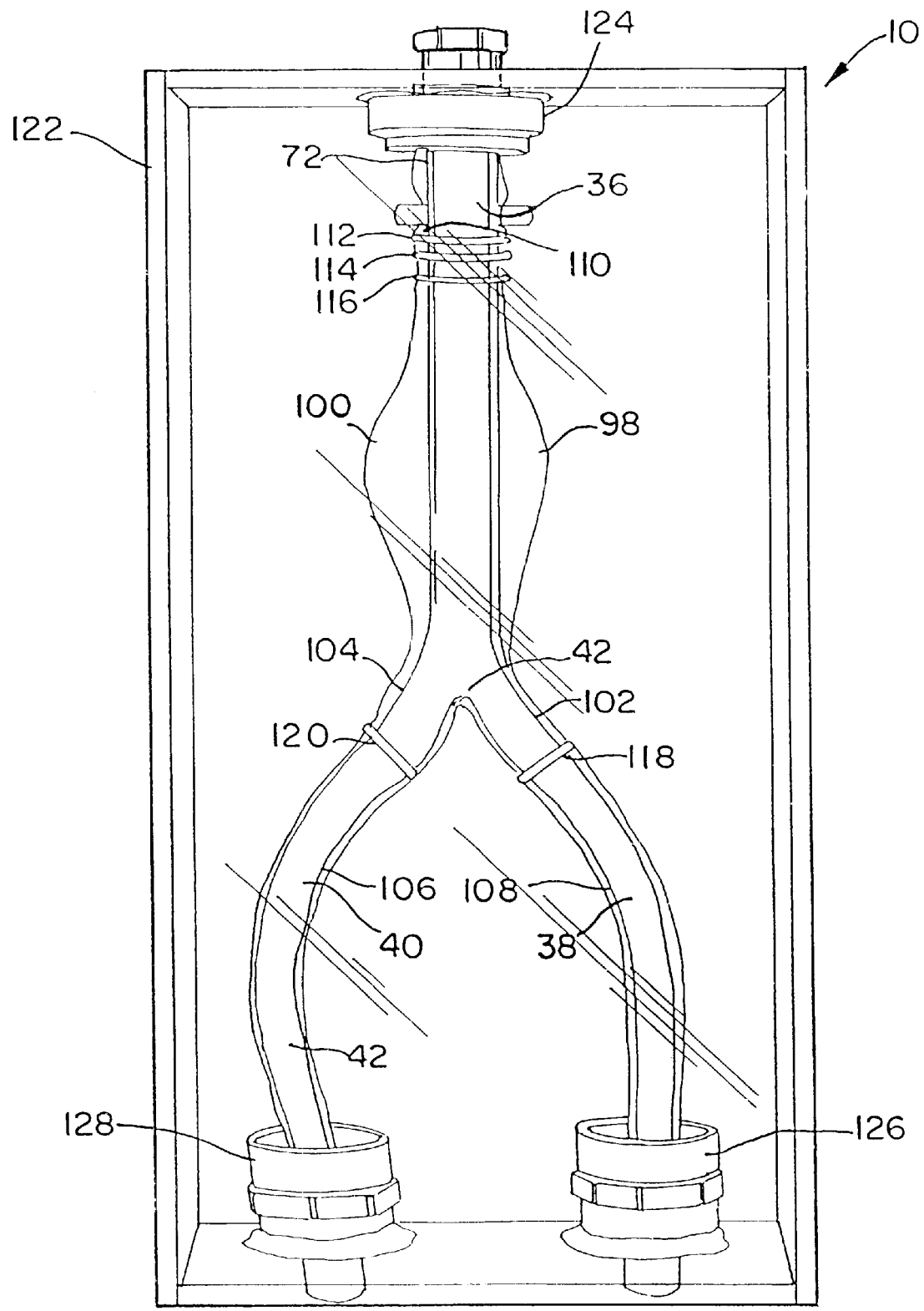
FIG. 10 is a front elevational view of the silicone aortic wall thickness and aneurysmal segments suspended in an acrylic box filled with silicone with one-way valves on the aortic and femoral ends.
Figure 11:
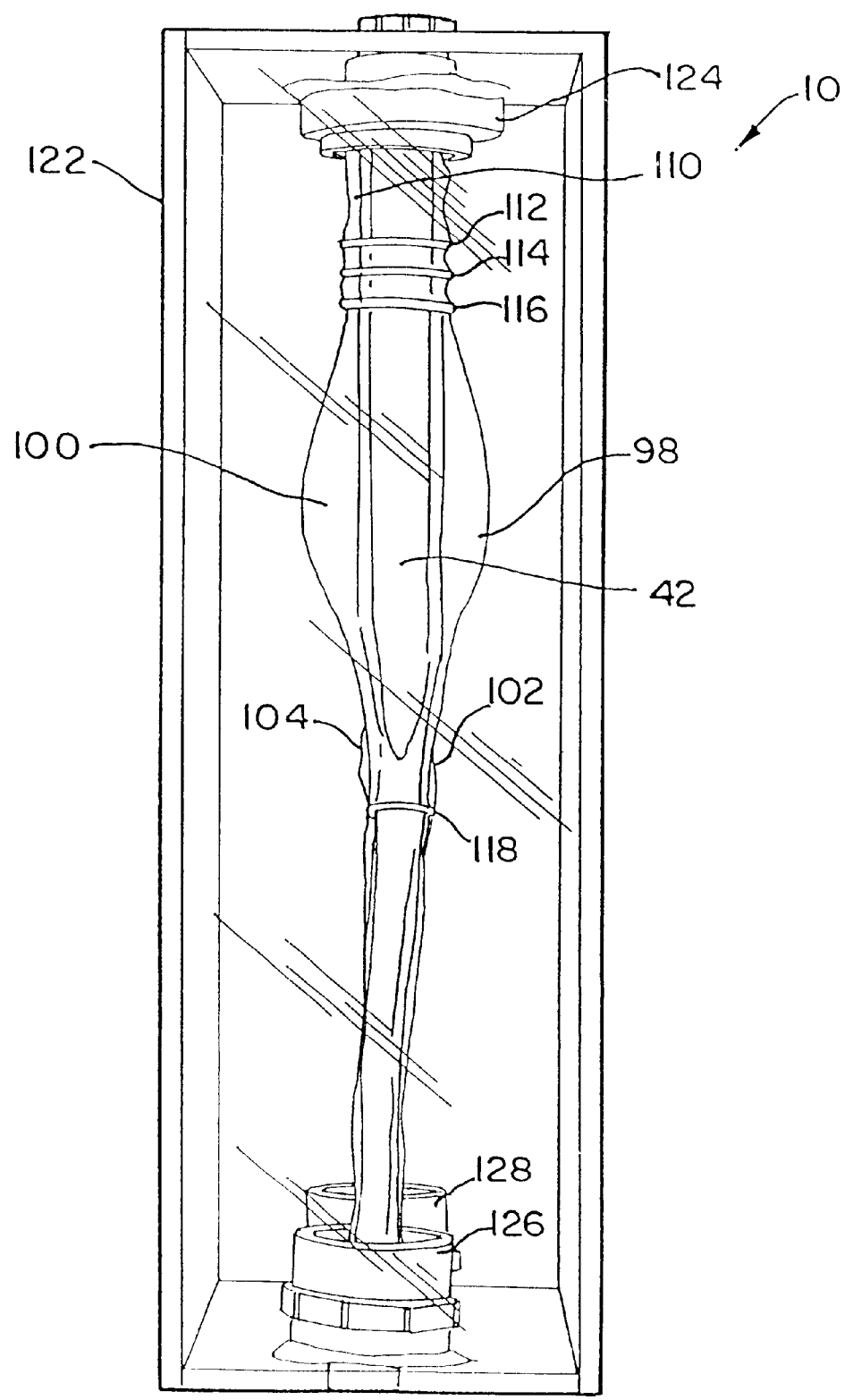
FIG. 11 is a side elevational view of the model shown in FIG. 10.
Figure 13:
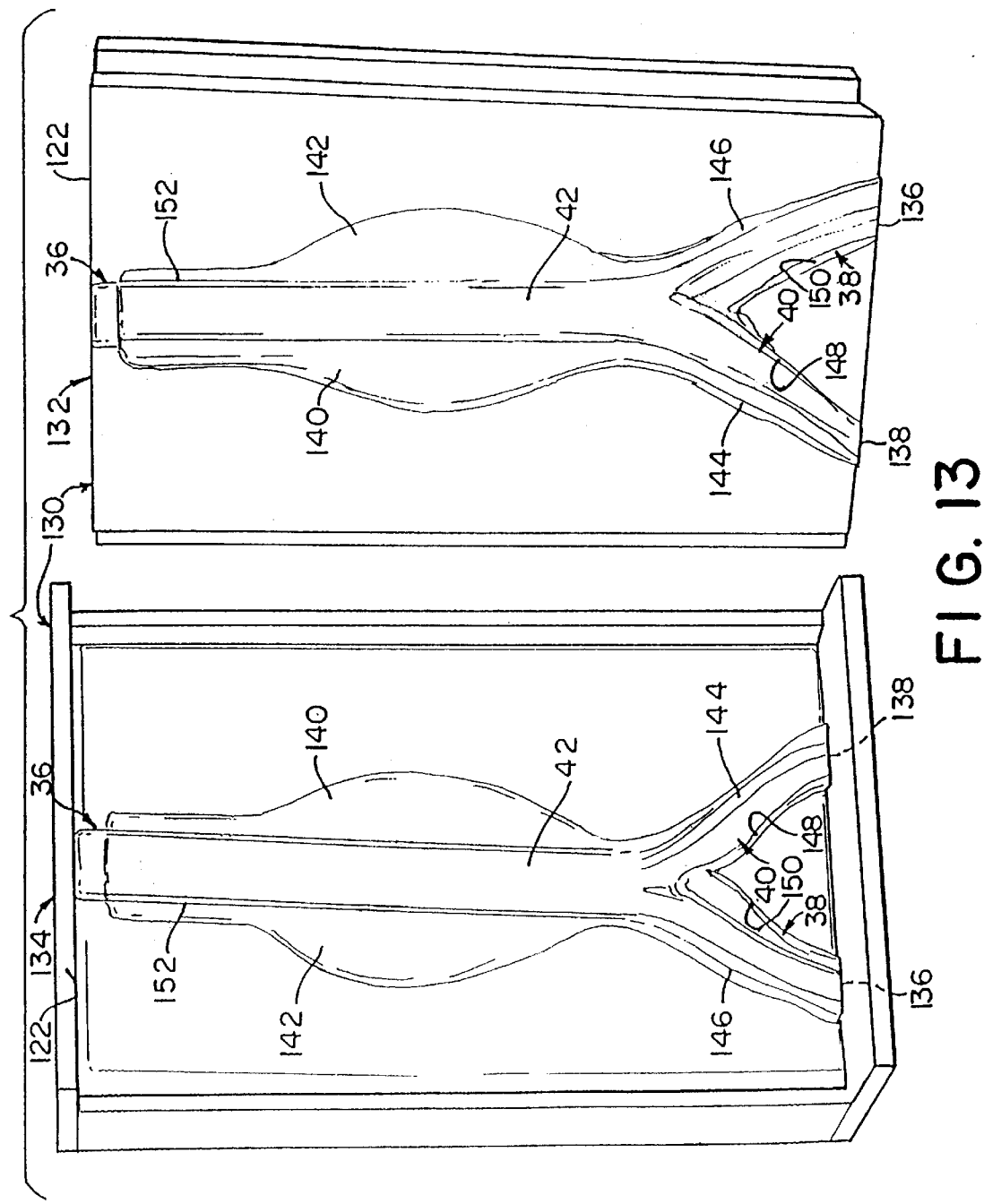
FIG. 13 is a front elevational view of an alternative embodiment of a stent-deploying training model showing the two mating sections of the training model in separated, open position.

Referring to FIGS. 10 and 11, an aortic stent-graft calibration model, generally designated 10, is provided for calibration of different testing modalities such as contrast aortography (CA), spiral computed tomography (CT), magnetic resonance imaging (MRI), and intravascular ultrasonography (IVUS). In an alternative embodiment, as shown in FIG. 13, an aortic stent-graft training model, generally designated 130, may be used for training purposes to simulate the introduction of a guidewire and catheter for deployment of a stent for repair of an abdominal aortic aneurysm (AAA). The training model 130 permits simulated deployment before the procedure is performed on a patient.

Generally, the aortic stent-graft calibration model 10 provides a full-size model simulating an abdominal aortic aneurysm (AAA). The model 10 includes a central core providing an aortic model shaped in the form of an aorta housing aneurysm. The aortic model portion of the calibration model 10 includes an arterial wall 110 and aneurysmal segments 98, 100, 102, 104, 106, 108, and 110 comprised of silicone. Marking indicia, such as rings 112, 114, 116, 118, and 120, are attached at selected locations on the aortic model 10 and filled with contrast agents, such as gadopentetate dimeglumine and iohexol, to permit accurate imaging by the imaging modalities. The aortic model is suspended in silicone contained within an acrylic box. A one-way valve 124 is located on the aortic end 36 and permits access to the lumen 42 of the aortic model for adding contrast agents or saline. Two one-way valves are located on the femoral ends 38 and 40 and allow access to the lumen 42 of the model for a 10 MHZ IVUS probe.

Figure 1:
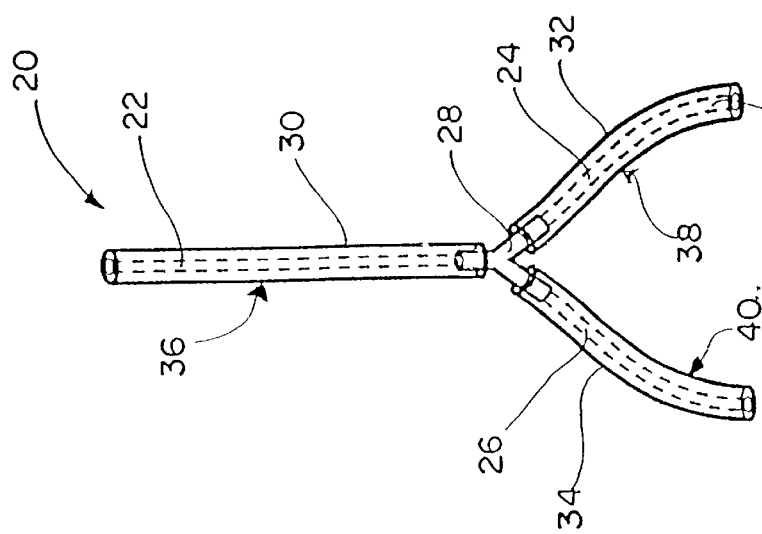
FIG. 1 is a schematic front perspective view of a rigid Y-frame of the model in accordance with the present invention.

Referring to FIG. 1, a Y-frame 20 is constructed from suitable rigid material, i.e. plastic piping, in a suitable size, i.e. 3 mm inside diameter, to form a temporary frame for creating the aortic model. The plastic piping is cut into three separate pieces 22, 24, and 26 of suitable length to form the shape of a Y for the Y-frame 20. A plastic Y-connector 28 serves to join the three pieces of the plastic piping 22, 24, and 26.

The inside diameter of the plastic piping is slightly larger than the outside diameter of the plastic Y-connector 28. This permits an end of the plastic piping to slide over an end of the plastic Y-connector 28 for a tight fit. The frame 20 is constructed by pushing the ends of the three pieces of plastic piping 22, 24, and 26 over the ends of the plastic Y-connector 28 to form the shape of a Y. The plastic Y-connector 28 serves to join the three pieces of plastic piping 22, 24, and 26.

Rubber tubing, in a suitable size, i.e. 3 mm inside diameter, encases the three pieces of plastic piping 22, 24, and 26. The rubber tubing is cut into three separate pieces 30, 32, and 34 of suitable length to encase the three pieces of plastic piping 22, 24, and 26. The three pieces of rubber tubing 30, 32, and 34 are worked upwards over the three pieces of plastic piping 22, 24, and 26 until the plastic Y-frame is tightly encased in rubber tubing. A trunk of the Y-frame represents the aortic neck 36 of the model 10 directed towards the heart of a human. Legs of the Y-frame represent the femoral arteries 38 and 40 directed towards the legs of a human.

Figure 2:
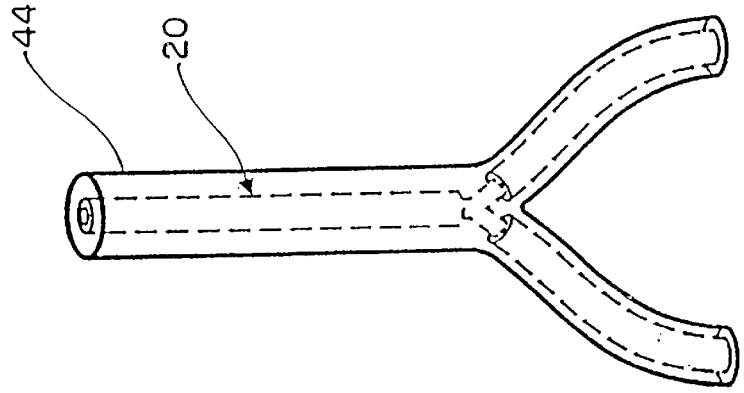
FIG. 2 is a schematic front perspective view of the rigid Y-frame shown in FIG. 1 with a coating material uniformly applied to its outer contour.

Referring to FIG. 2, hot wax is utilized to add thickness to the contour of the rigid Y-frame 20. Hot wax is applied uniformly to the outer contour of the rigid Y-frame 20 to achieve an outer diameter equal to the desired final inner diameter of the lumen of the completed aortic model. The hot wax is left to cool to form a hardened wax contour 44 for the Y-frame 20.

Figure 3:
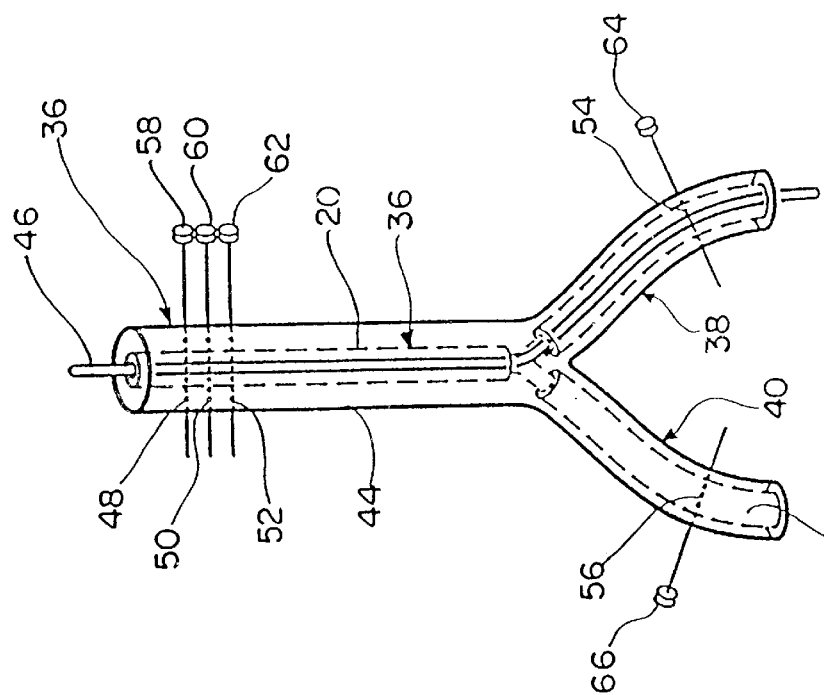
FIG. 3 is a schematic front perspective view of the rigid Y-frame shown in FIG. 2 with apertures through selected locations on the Y-frame and an intraluminal catheter inserted through the femoral end.

As shown in FIG. 3, marking indicia are made at selected locations on the Y-frame 20 for marking the sites for dimension measurements. A catheter 46 of suitable size, i.e. 2 mm, is passed though the lumen 42 of the model 10. Apertures 48, 50, 52, 54, and 56 of suitable size, i.e. 0.125 cm diameter, are formed through selected locations of the hardened wax contour 44, Y-frame 20, and catheter 46.

Three of the apertures 48, 50, and 52 are in the aortic neck 36 of the wax-coated Y-frame of the aortic model and are located relatively close together. The other two apertures 54 and 56 are respectively located in each of the femoral arteries 38 and 40 of the wax-coated Y-frame.

After the apertures 48, 50, 52, 54, and 56 are made, the catheter 46 is withdrawn from the lumen 42 of the aortic model and the distances between the apertures 48, 50, 52, 54, and 56 on the catheter 46 are measured. These measurements determine the actual lengths which provide the standard against which the measurements from the images of the model from the imaging modalities will be compared after each imaging modality is performed on the aortic model.

After the catheter 46 is withdrawn from the lumen 42 of the model 10 and the selected distances are measured, extra long pins 58, 60, 62, 64, and 66 are passed through the apertures 48, 50, 52, 54, and 56 of the wax-coated Y-frame 20 to mark the apertures more clearly. The pins 58, 60, 62, 64, and 66 are similar to needles used for spinal taps in the medical field and, thus, are very long and very thin.

Referring to FIG. 4, a one-piece mold 76 is formed about the wax-coated Y-frame 20. The wax-coated Y-frame 20, with pins 58, 60, 62, 64, and 66, is placed in a rectangular shaped box 68 with a top 70 open to the air. The height of the box 68 is equal to the height of the wax-coated Y-frame 20. Tin-based silicone elastomer is poured into the open top 70 of the rectangular shaped box 68 and around the wax-coated Y-frame 20 with pins 58, 60, 62, 64, and 66. Tin-based silicone elastomer is used because it has the special characteristic of not sticking to wax or polyurethane.

The tin-based silicone elastomer fills the entire rectangular shaped box 69 until it reaches the open top 70 without spilling over, leaving the end of an aortic neck 72 of the wax-coated Y-frame 20 open to the air. The tin-based silicone elastomer is left to harden in the rectangular shaped box 68 forming the one-piece mold 76.

After the tin-based silicone elastomer hardens in the mold 76, the wax coated Y-frame 20 and pins 58, 60, 62, 64, and 66 are removed from the one-piece mold 76. To effect such removal, soapy water is poured in between the aortic neck 72 of the wax-coated Y-frame 20 and the one-piece silicone mold 76 to provide lubrication between the wax-coated Y-frame 20 and the tin-based silicone elastomer mold 76. As one pulls and wiggles the aortic neck 72 of the wax coated Y-frame 20 embedded in the mold 76, the wax coated Y-frame 20 with pins 58, 60, 62, 64, and 66 slides out of the mold 76. The ease of removing the wax coated Y-frame 20 and pins 58, 60, 62, 64, and 66 from the silicone mold 76 is facilitated by the special non-stick characteristics between silicone and wax.

A hollow one-piece silicone mold 76 of the Y-frame 20 with an outside diameter equal to the desired final inside diameter of the lumen 42 of the aortic model remains. The hollow one-piece silicone mold 76 contains impressions of the pins 58, 60, 62, 64, and 66 which mark the sites for dimension measurements. The pins 58, 60, 62, 64, and 66 are removed from the wax-coated Y-frame 20 and reinserted back into the impressions of such pins in of the mold 76. Liquid polyurethane is their poured into the one-piece silicone mold 76 and allowed to cool.

After the polyurethane in the one-piece silicone mold 76 is allowed to cool, it hardens into a flexible, solid polyurethane core 74. The pins 58, 60, 62, 64, and 66 are removed from the solid core 74 and one-piece silicone mold 76. Soapy water is poured in between the aortic neck 72 of the polyurethane core 74 and the one-piece silicone mold 76 to provide lubrication between the core 74 and the mold 76. As one pulls and wiggles the aortic neck 72 of the polyurethane core 74 embedded in the mold 76, the polyurethane core 74 slides out of the mold 76. The ease of removing the polyurethane core 74 from the silicone mold 76 is facilitated by the special non-stick characteristics between silicone and polyurethane.

As shown in FIG. 5, the flexible, polyurethane core 74 remains with impressions from the apertures 48, 50, 52, 54, and 56 through which the pins 58, 60, 62, 64, and 66 had been inserted. Using these impressions, the pins 58, 60, 62, 64, and 66 are reinserted back into the polyurethane core 74.

Figure 7:
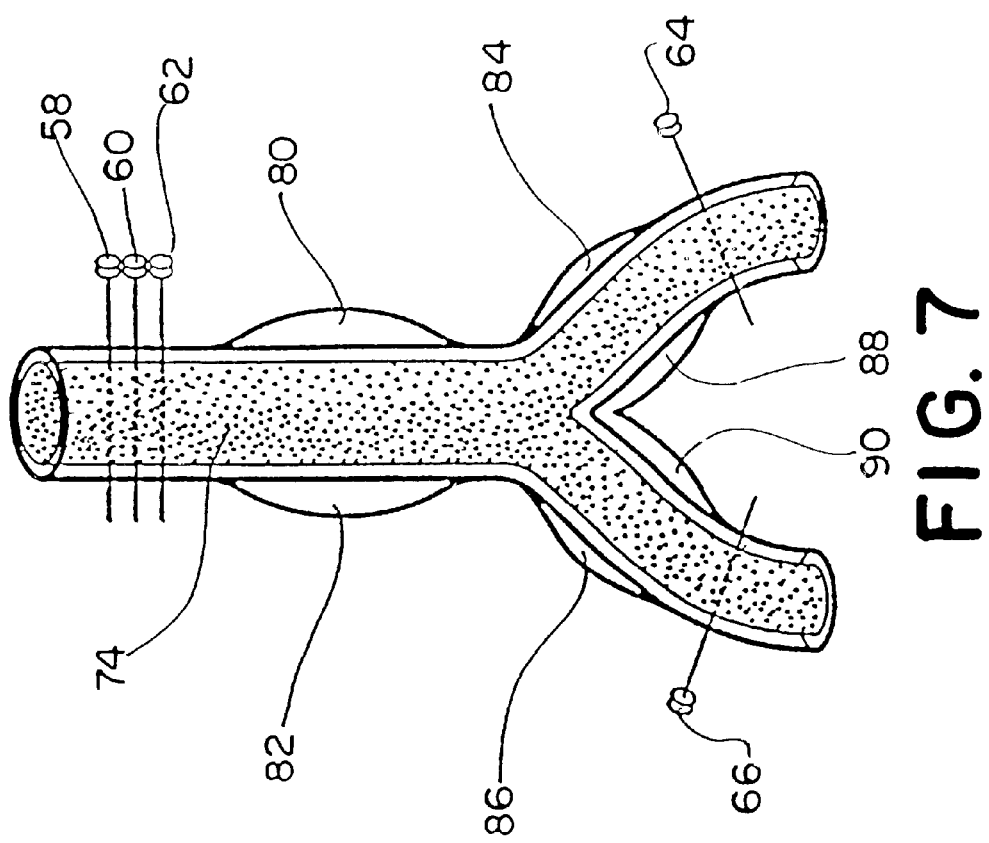
FIG. 7 is a schematic front perspective view of the coated solid core shown in FIG. 6 with additional coating material applied to selective locations on the outer contour to provide aneurysmal segments.
Figure 6:
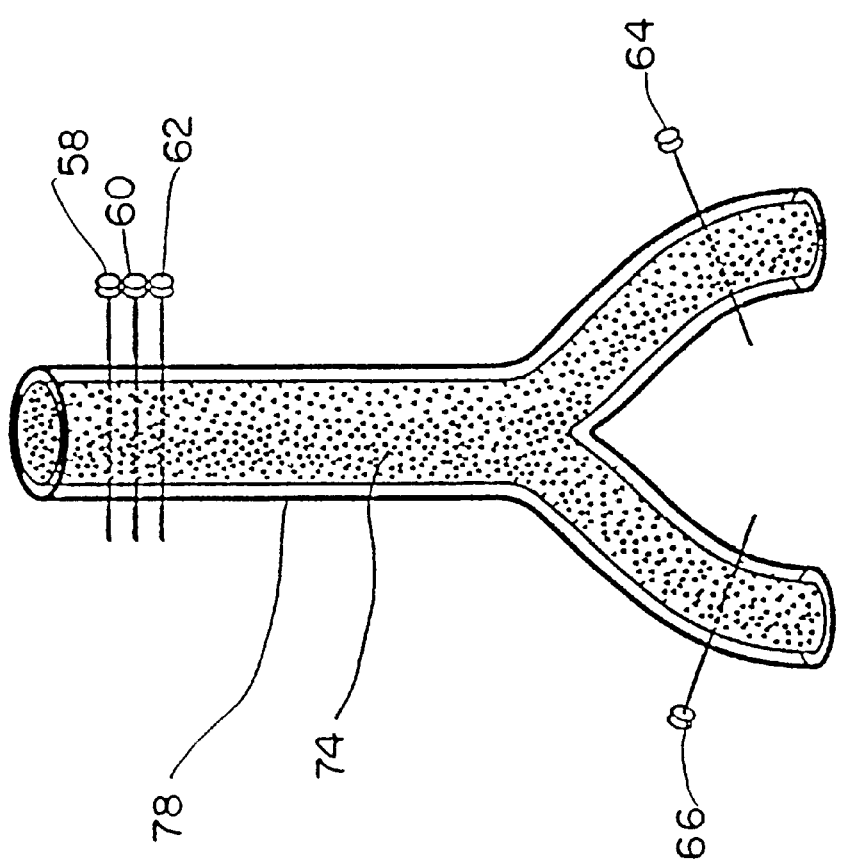
FIG. 6 is a schematic front perspective view of the solid core shown in FIG. 5 with a coating material uniformly applied to its outer contour to provide a uniform arterial wall thickness.

Referring to FIGS. 6 and 7, hot wax is utilized to add an arterial wall 78 and aneurysmal segments 80, 82, 84, 86, 88, and 90 to the outer contour of the flexible, solid polyurethane core 74. Hot wax is applied to the outer contour of the solid polyurethane core 74 and around pins 58, 60, 62, 64, and 66 to achieve the desired final thickness of the arterial wall 78 of the aortic model. A suitable thickness for the arterial wall 78 is 2–4 mm. Additionally, hot wax is applied at selected locations and shapes to the outer contour of the coated solid polyurethane core 74 and around pins 58, 60, 62, 64, and 66 to build the aneurysmal segments 80, 82, 84, 86, 88, and 90 of the completed aortic model. Suitable thickness for the aneurysmal segments 80, 82, 84, 86, 88, and 90 is 14–16 mm. The hot wax is left to cool so that an arterial wall 78 and aneurysmal segments 80, 82, 84, 86, 88, and 90 of hardened wax is formed on the solid polyurethane core 74.

Referring to FIG. 8, a two-piece polyurethane mold 92 is formed about the wax-coated solid polyurethane core 74 and pins 58, 60, 62, 64, and 66. The solid polyurethane core 74, with pins 58, 60, 62, 64, and 66, having the wax-coated arterial wall 78 and aneurysmal segments 80, 82, 84, 86, 88, and 90, is laid horizontally in the bottom of an acrylic box 94. The bottom of the acrylic box 94 has an open top. A portion of the solid polyurethane core 74 protrudes out of the open top of the bottom of the acrylic box 94. The bottom of the acrylic box 94 is filled with liquid polyurethane. The liquid polyurethane is allowed to dry and harden. A suitable chemical that prevents polyurethane from sticking to itself, i.e. silicone oil, is applied to the exposed surface of the hardened polyurethane.

The top of the acrylic box 96 is in the form of a collar having an open top and bottom. The acrylic top 96 is placed on the bottom of the acrylic box 94 containing the hardened polyurethane and partially imbedded wax-coated polyurethane core 74. The top and bottom of the box seal together. Liquid polyurethane is then poured into the open top of the top 96 of the acrylic box. The polyurethane is allowed to dry and harden.

After the two-piece polyurethane mold 92 hardens, the top and bottom of the acrylic box 94 and 96 are pulled apart. The two polyurethane sections in the respective top and bottom of the acrylic box 94 and 96 do not stick together and are easy to separate because the chemical, i.e. silicone oil, applied to the exposed surface of the hardened polyurethane section in the bottom of the box prevents the two polyurethane sections 94 and 96 from sticking to each other as the polyurethane hardens in to the top of the box. After separating the two-piece mold 92, the wax-coated polyurethane core 74, with the wax arterial wall 78 and aneurysmal segments 80, 82, 84, 86, 88, and 90, is removed from mold 92. A two-piece polyurethane mold 92 having an impression of the polyurethane core 74 within the wax-coated arterial wall 78 and aneurysmal segments 80, 82, 84, 86, 88, and 90 remains.

The wax coatings form the arterial wall 78 and aneurysmal segments 80, 82, 84, 86, 88, and 90 are removed from the polyurethane core 74. Additionally, the pins 58, 60, 62, 64, and 66 are removed from the polyurethane core 74. The polyurethane core 74 is then placed back in the two-piece polyurethane mold 92 leaving an empty space where the wax arterial wall 78 and aneurysmal segments 80, 82, 84, 86, 88, and 90 previously existed. The pins 58, 60, 62, 64, and 66 are then reinserted through the two-piece polyurethane mold 92 and the polyurethane core 74 to hold the first and second halves of the polyurethane filled acrylic box 94, 96 together.

The empty space where the wax arterial wall 78 and aneurysmal segments 80, 82, 84, 86, 88, and 90 previously existed is then filled with silicone. This is achieved by squeezing silicone between the end of the aortic neck 72 of the polyurethane core 74 and the two-piece polyurethane mold 92 creating a silicone filled arterial wall 110 and aneurysmal segments 100, 102, 104, 106, 108, and 110. After the silicone is allowed to dry, the pins 58, 60, 62, 64, and 66 are removed and the two halves 94, 96 of the two-piece polyurethane mold 92 are separated. The polyurethane core 74, with the silicone filled arterial wall 110 and aneurysmal segments 100, 102, 104, 106, 108, and 110, is removed from the two-piece polyurethane mold 92.

The pins 58, 60, 62, 64, and 66 are then reinserted through the polyurethane core 74 and the silicone filled arterial wall 110 and aneurysmal segments 100, 102, 104, 106, 108, and 110. Suitable polyurethane marking rings 112, 114, 116, 118, and 120, i.e. 25 gauge butterfly tubing, are fixed at the site of the marker holes directly above the pins 58, 60, 62, 64, and 66 in the polyurethane core 74. The pins 58, 60, 62, 64, and 66 are then removed leaving the polyurethane marking rings 112, 114, 116, 118, and 120 attached to the aortic neck 36 and at aneurysmal/nonaneurysmal junction of the iliacs as illustrated in FIG. 9. The polyurethane marking rings 112, 114, 116, 118, and 120 are used as reference points for dimension measurements by the various imaging modalities.

The polyurethane marking rings 112, 114, 116, 118, and 120 may be filled with a suitable contrast agent such as 148 mg/ml iohexol and 4.64 mg/ml gadopentetate dimeglumine to enhance the visibility of the imaging techniques. The concentrations of iohexol and gadopentetate dimeglumine were chosen after repeated pilot imaging trials with various concentrations and were discovered to be a suitable combination for all four imaging techniques.

The polyurethane core 74 with the silicone arterial wall 110 and aneurysmal segments 100, 102, 104, 106, 108, and 110, and polyurethane marking rings 112, 114, 116, 118, and 120, is fixed at its aortic end 36 and femoral ends 38, 40 in an acrylic box 122 with an open top. The aortic end 36 and femoral ends 38 and 40 of the aortic model are attached to the acrylic box 122 by suitable fittings, i.e. standard plumbers fittings 124, 126, and 128. Suitable one-way valves, i.e. catheter valves are located inside the fittings 124, 126, and 128. The one-way valve at the aortic end 36 allows access to the lumen 42 of the aortic model for filling the lumen 42 with saline or contrast agents. The one-way valves at the femoral ends 38 and 40 allow a catheter to access the lumen 42 of the aortic model for angiographic catheters and IVUS probes.

The acrylic box 122 is filled to the top with suitable clear silicone such as a silicone used for breast implants. After the silicone dries, soapy water is poured between the end of the aortic neck 72 of the polyurethane core 74 and the silicone arterial wall coating 110 to provide lubrication therebetween. As one pulls and wiggles the aortic neck 72 of the polyurethane core 74 embedded in the silicone filled acrylic box 122, the polyurethane core 74 slides out of the silicone filled acrylic box 122 leaving the silicone aortic wall and aneurysm embedded in the silicone filled acrylic box 122. The ease of removing the polyurethane core 74 from the silicone filled acrylic box 122 is due to the special non-stick characteristics between silicone and polyurethane.

After the polyurethane core 74 is removed, the hollow lumen 42 with the silicone arterial wall 110 and aneurysmal segments 100, 102, 104, 106, 108, and 110, and polyurethane marking rings 112, 114, 116, 118, and 120 are suspended in a silicone gel contained within the acrylic box 122 to complete the aortic stent-graft calibration model 10 as shown in FIGS. 10 and 11.

The aortic stent-graft calibration model 10 can be utilized to calibrate the equipment of different imaging modalities to ensure accuracy. The model 10 can be imaged by contrast aortography (CA), spiral computed tomography (CT), magnetic resonance imaging (MRI), and intravascular ultrasonography (IVUS).

The polyurethane marking rings 112, 114, 116, 118, and 120 are attached to selected locations on the model 10 and filled with a suitable contrast agent such as 148 mg/ml iohexol and 4.64 mg/ml gadopentetate dimeglumine as discussed above. The concentrations of iohexol and gadopentetate dimeglumine were discovered to be a suitable combination for all four imaging techniques.

The four imaging modalities are then performed on the model. Each measurement obtained from the imaging modalities is compared to the actual dimensions of the model as determined during its construction. The equipment of each imaging modality can then be calibrated accordingly.

Figure 12:
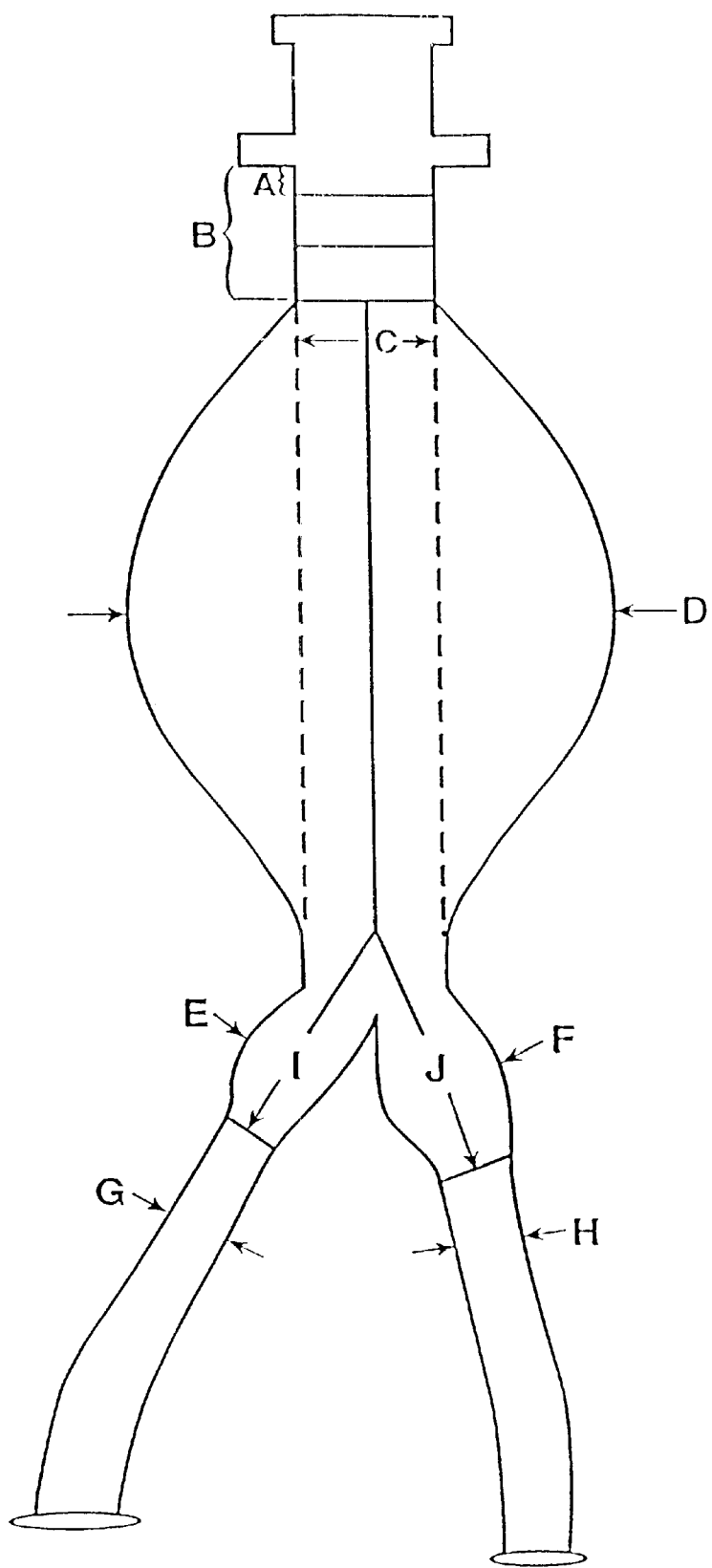
FIG. 12 is a schematic front elevational view of the model indicating sites of measurement for different imaging modalities.

As shown in FIG. 12, ten dimension measurements of the model 10 are recorded by the four imaging modalities. The dimension measurements are represented by letters on FIG. 12 and are defined as follows: (A) is the distance from the caudad edge of the renal artery to the uppermost marking ring 112; (B) is the distance from the lower edge of the renal artery to the cephalad origin of the abdominal aortic aneurysm (AAA); (C) is the diameter of the aortic lumen 42; (D) is the maximum outside diameter of the abdominal aortic aneurysm (AAA); (E) is the maximum outside diameter of the right common iliac aneurysm; (F) is the maximum outside diameter of the left common iliac aneurysm; (G) is an outer diameter of a parallel segment of nonaneurysmal right iliac arteries; (H) is an outer diameter of a parallel segment of nonaneurysmal left iliac arteries; (I) is a centerline luminal length from a caudad edge of the renal artery to the respective iliac ring of an aorto-right-iliac segment which would simulate the stent-graft length required to anchor the graft in a normal aorta (represented by the infrarenal segment above the third ring 116) and a normal iliac (represented by the iliac segment below the iliac rings); and (J) is a centerline luminal length from a caudad edge of the renal artery to the respective iliac ring of an aorto-left-iliac segment which would simulate the stent-graft length required to anchor the graft in a normal aorta (represented by the infrarenal segment above the third ring 116) and a normal iliac (represented by the iliac segment below the iliac rings).

FIG. 13 illustrates an embodiment of the present invention in which the aortic stent-graft model 130 may be used for training purposes. This training model 130 simulates the introduction of a guidewire and catheter for deployment of a stent for repair of an abdominal aortic aneurysm (AAA). This permits simulation on the training model 130 before the procedure is performed on a patient. The training model 130 is comprised of two separate sections 132 and 134 that may be repetitiously opened to allow access to the stent after deployment.

The training model 130 for stent deployment is made separately from the calibration model 10 discussed above. Both models are manufactured similarly up to FIG. 8. Thus, the steps that are similar for both the calibration model 10 and the training model 130 discussed above will not be repeated. A difference in manufacture of the training model 130 is that no marking rings 112, 114, 116, 118, and 120 are used. Additionally, the training model 130 is left as the two piece polyurethane mold 92 discussed above.

The steps that differ between the manufacture of the calibration model 10 and training model 130 are discussed in detail below. Referring to FIG. 8, the two piece polyurethane mold 92 is formed about the solid polyurethane core 74 and the wax arterial wall 78 and aneurysmal segments 80, 82, 74, 86, 88, and 90. The solid polyurethane core 74 with the wax arterial wall 78 and aneurysmal segments 80, 82, 84, 86, 88, and 90, is laid horizontally in the bottom 94 of an acrylic box. The bottom 94 of the acrylic box has an open top. A portion of the solid polyurethane core 74 protrudes out of the open top of the bottom 94 of the acrylic box. The bottom 94 of the acrylic box is then filled with liquid polyurethane. The liquid polyurethane is allowed to dry and harden. A suitable chemical that prevents polyurethane from sticking to itself, i.e. silicone oil, is applied to the exposed surface of the hardened polyurethane.

The top 96 of the acrylic box is in the form of a collar. The top 96 is placed on the bottom 94 of the acrylic box containing the hardened polyurethane and partially imbedded polyurethane core 74. The top 96 and bottom 94 seal together. Liquid polyurethane is then poured into the open top of the top 96 of the acrylic box. The polyurethane is allowed to dry and harden.

After the two-piece polyurethane mold 92 hardens, the top 96 and bottom 94 of the acrylic box are pulled apart. The top 96 and bottom 94 of the acrylic box do not stick together and are easy to separate due to the chemical, i.e. silicone oil, applied to the exposed surface of the hardened polyurethane in the bottom 94 of the box. After separating the two-piece mold 92, the polyurethane core 74, with the wax arterial wall 78 and aneurysmal segments 80, 82, 84, 86, 88, and 90, is removed. An impression of the polyurethane core 74 and the wax arterial wall 78 and aneurysmal segments 80, 82, 84, 86, 88, and 90 remains in the two-piece mold 92.

The wax arterial wall 78 and aneurysmal segments 80, 82, 84, 86, 88, and 90 are removed from the polyurethane core 74. A suitable substance, i.e. petroleum jelly, is applied to the surface of the polyurethane core 74 to prevent polyurethane from sticking to itself. The jelly coated polyurethane core 74 is placed back in the section of the two-piece polyurethane mold 92 housed in the bottom 94 of the acrylic boxes leaving an empty space where the wax arterial wall 78 and aneurysmal segments 80, 82, 84, 86, 88, and 90 previously existed.

The empty space where the wax arterial wall 78 and aneurysmal segments 80, 82, 84, 86, 88, and 90 previously existed in the selected section of the mold, is filled with liquid polyurethane. A polyurethane filled arterial wall 152 and aneurysmal segments 140, 142, 144, 146. 148, and 150 are created. Red die can be mixed with the polyurethane before filling the arterial wall 152 and aneurysmal segments 140, 142, 144, 146, 148, 150 of the training model 130 so that they can be easily seen in the polyurethane filled acrylic box. After the polyurethane is allowed to dry, the polyurethane core 74, is removed from the selected section of the two-piece polyurethane mold 92. The polyurethane core 74 is easy to remove from the polyurethane arterial wall 152 and aneurysmal segments 140, 142, 144, 146, 148, and 150 due to the substance, i.e. petroleum jelly, applied to the surface of the polyurethane core 74. The remaining polyurethane arterial wall 152, aneurysmal segments 140, 142, 144, 146, 148, and 150 and hollow lumen 42 suspended in the polyurethane contained in the bottom of the acrylic box comprise one section 132 of the training model as shown in FIG. 13.

After the first section 132 of the training model is created, the second section 134 is created in a similar manner. The polyurethane core 74 is removed from the bottom 94 of the acrylic box and petroleum jelly is again applied to the surface of the polyurethane core 74. The polyurethane core 74 is then placed in the section of the two-piece polyurethane mold 92 in the top of the acrylic box leaving an empty space where the wax arterial wall 78 and aneurysmal segments 80, 82, 84, 86, 88, and 90 previously existed.

The empty space where the wax arterial wall 78 and aneurysmal segments 80, 82, 84, 86, 88, and 90 previously existed in the top 96 of the acrylic box is filled with liquid polyurethane to create the polyurethane arterial wall 152 and aneurysmal segments 140, 142, 144, 146, 148, and 150 in the mold section in the top 96 of the acrylic box. Red die can be mixed with the polyurethane before filling the arterial wall 152 and aneurysmal segments 140, 142, 144, 146, 148, and 150 of the training model 130 so that they can be easily seen in the polyurethane filled acrylic box. After the polyurethane is allowed to dry, the polyurethane core 74, is removed from the top of the acrylic box containing the second section of the two-piece polyurethane mold 92. Once again, the polyurethane core 74 is easy to remove from the polyurethane arterial wall 152 and aneurysmal segments 140, 142, 144, 146, 148, and 150 due to the substance, i.e. petroleum jelly, applied to the surface of the polyurethane core 74. The remaining polyurethane arterial wall 152, the aneurysmal segments 140, 142, 144, 146, 148, and 150 and the hollow lumen 42 in the section of the mold contained in the top of the acrylic box comprise the second section 134 of the training model as shown in FIG. 13.

Therefore, the training model 130 is comprised of two separate sections 132 and 134 that may repeatedly be put together and separated to allow access to the stent after deployment. The first section 132 and second section 134 of the training model 130 are held together by suction between the two solid polyurethane mold sections 132 and 134. Access to the lumen 42 of the training model 130 for deployment of a stent is effected through open ends 136 and 138 at the femoral ends 38 and 40 of the training model 130.

To simulate the repair of an abdominal aortic aneurysm (AAA) on the training model 130, a guidewire and catheter are introduced into one of the open ends 136 and 138 on the femoral end 38 and 40 of the model 130. The open ends 136 and 138 permit the guidewire and catheter to access the lumen 42 of the model 130. When the user determines that the guidewire and catheter are in the correct location of the lumen 42 of the aorta, the stent is deployed. When the whole procedure is finished, the first section 132 and second section 134 of the training model 130 may be pulled apart until the suction that holds the training model 130 together is released. When the training model 130 is separated into two pieces, the exact location of the stent may be checked by direct inspection of the model. The stent can be retrieved and the two sections of the training model can be pressed back together for additional practice.

It will be recognized by those skilled in the art that changes or modifications may be made to the above-described embodiments without departing from the broad inventive concept of the invention. It should therefore be understood that this invention is not limited to the particular embodiments described herein but is intended to include all changes and modifications that are within the scope and spirit of the invention as set forth in the claims.

What is claimed is:

1. An abdominal aortic aneurysm model, comprising:
   (a) an arterial wall formed about a central lumen;
   (b) aneurysmal segments formed on the arterial wall; and
   (c) marking indicia for marking selected sites for selected dimension measurements on the arterial wall and aneurysmal segments, wherein the marking indicia are detectable upon imaging of the model to determine discrepancies in measurements between selected sites on the model and images of the selected sites upon the imaging of the model.

2. A model according to claim 1, wherein the marking indicia include markers positioned external to the lumen.

3. A model according to claim 1, wherein the marking indicia are detectable by magnetic resonance imaging, computed tomography, contrast aortography, and intravascular ultrasonography.

4. A model according to claim 1, wherein the marking indicia are detectable by at least one of magnetic resonance imaging, computed tomography, contrast aortography, and intravascular ultrasonography.

5. A model according to claim 1, wherein the marking indicia include a contrast agent.

6. A model according to claim 5, wherein the contrast agent includes at least one of gadopentetate dimeglumine and iohexol.

7. A model according to claim 1, comprising an aortic neck and wherein at least one marking indicia is located at the aortic neck.

8. A model according to claim 7, comprising a femoral artery and wherein at least one marking indicia is located at the femoral artery.

9. A model according to claim 1, comprising a femoral artery and wherein at least one marking indicia is located at the femoral artery.

10. A model according to claim 1, comprising two femoral arteries and wherein at least one marking indicia is located at each of the two femoral arteries.

11. A model according to claim 1, comprising an aortic neck and wherein at least two marking indicia are located at the aortic neck.

12. A model according to claim 11, comprising a femoral artery and wherein at least one marking indicia is located at the femoral artery.

13. An abdominal aortic aneurysm model comprising:
    (a) a lumen for insertion of a guidewire and catheter for deployment of a stent;
    (b) arterial walls formed about the lumen;
    (c) aneurysmal segments formed at the arterial walls; and
    (d) an outer support for the arterial walls and the aneurysmal segments separable into two mating sections held together by suction.

14. An abdominal aortic aneurysm model, comprising:
    (a) an arterial wall formed about a central lumen;
    (b) aneurysmal segments formed on the arterial wall; and
    (c) annular marking indicia surrounding the central lumen for marking selected sites for selected dimension measurements on the arterial wall and aneurysmal segments, wherein the marking indicia are detectable upon imaging of the model to determine discrepancies in measurements between selected sites on the model and images of the selected sites upon the imaging of the model.

15. An abdominal aortic aneurysm model, comprising:
    (a) an arterial wall formed about a central lumen;
    (b) aneurysmal segments formed on the arterial wall; and
    (c) marking indicia positioned external to the lumen for marking selected sites for selected dimension measurements on the arterial wall and aneurysmal segments, wherein the marking indicia are detectable by at least one of magnetic resonance imaging, computed tomography, contrast aortography, and intravascular ultra-sonography to determine discrepancies in measurements between selected sites on the model and images of the selected sites upon the imaging of the model.

16. The abdominal aortic aneurysmal model of claim 15 wherein the marking indicia include a contrast agent detectable by all of magnetic resonance imaging, computed tomography, contrast aortography, and intravascular ultra-sonography.

17. An abdominal aortic aneurysm model, comprising:

(a) an arterial wall formed about a central lumen;

(b) aneurysmal segments formed on the arterial wall; and (c) annular marking indicia positioned external to the lumen for marking selected sites for selected dimension measurements on the arterial wall and aneurysmal segments, wherein the marking indicia are detectable upon imaging of the model to determine discrepancies in measurements between selected sites on the model and images of the selected sites upon the imaging of the model, and wherein the marking indicia include a contrast agent.

18. An abdominal aortic aneurysm model, comprising:

(a) an arterial wall formed about a central lumen;

(b) aneurysmal segments formed on the arterial wall;

(c) marking indicia for marking selected sites for selected dimension measurements on the arterial wall and aneurysmal segments, wherein the marking indicia are detectable upon imaging of the model to determine discrepancies in measurements between selected sites on the model and images of the selected sites upon the imaging of the model;

(d) a housing; and (e) a gel within the housing for suspending the arterial wall within the housing, with the gel external to the arterial wall.

19. A model according to claim 18, wherein the marking indicia include at least one annular ring surrounding the central lumen.

20. A model according to claim 18, wherein the marking indicia are detectable by magnetic resonance imaging, computed tomography, contrast aortography, and intravascular ultrasonography.

21. A model according to claim 18, wherein the marking indicia are detectable by at least one of magnetic resonance imaging, computed tomography, contrast aortography, and intravascular ultrasonography.

22. A model according to claim 18, wherein the marking indicia include a contrast agent.

23. A model according to claim 22, wherein the contrast agent includes at least one of gadopentetate dimeglumine and iohexol.

24. A model according to claim 18, comprising an aortic neck and wherein at least one marking indicia is located at the aortic neck.

25. A model according to claim 18, comprising a femoral artery and wherein at least one marking indicia is located at the femoral artery.

26. A model according to claim 18, comprising two femoral arteries and wherein at least one marking indicia is located at each of the two femoral arteries.

27. A model according to claim 18, comprising an aortic neck and wherein at least two marking indicia are located at the aortic neck.

28. A model according to claim 27, comprising a femoral artery and wherein at least one marking indicia is located at the femoral artery.

29. A model according to claim 24, comprising a femoral artery and wherein at least one marking indicia is located at the femoral artery.

* * * * *